United States Patent [19]

Condon et al.

[11] Patent Number: 5,318,946
[45] Date of Patent: Jun. 7, 1994

[54] 2-(HETEROARYLOXYPHENOXY)ALKYL-SULFONATES USEFUL AS HERBICIDAL AGENTS

[75] Inventors: Michael E. Condon, Lawrenceville; Michael A. Guaciaro, Hightstown, both of N.J.

[73] Assignee: American Cyanamid Company, Wayne, N.J.

[21] Appl. No.: 800,673

[22] Filed: Nov. 27, 1991

[51] Int. Cl.$^5$ ............... A01N 43/40; C07D 213/643; C07D 213/85; C07F 1/08
[52] U.S. Cl. .......................... 504/244; 546/6; 546/288; 546/294; 546/302; 544/318; 544/354; 548/152; 548/221; 548/306.4
[58] Field of Search ............ 546/294, 6, 288; 504/244

[56] References Cited

U.S. PATENT DOCUMENTS 4,661,149 4/1987 Raju .................... 504/195

FOREIGN PATENT DOCUMENTS 1572125 7/1980 United Kingdom ............ 504/352

Primary Examiner—Alan L. Rotman
Attorney, Agent, or Firm—John W. Hogan, Jr.

[57] ABSTRACT 2-(Heteroaryloxyphenoxy)alkylsulfonate compounds which are effective for the selective control of grass weed species in the presence of crops are described. Also described are a method for the selective herbicidal use of the compounds and a method for their preparation.

10 Claims, No Drawings

2-(HETEROARYLOXYPHENOXY)ALKYLSULFONATES USEFUL AS HERBICIDAL AGENTS

BACKGROUND OF THE INVENTION

Grass weeds cause trememdous global economic losses by reducing crop yields and lowering crop values. In particular, blackgrass, barnyardgrass, green foxtail and wild oats cause extensive economic losses worldwide. In addition some herbicides have caused some crop damage due to inadvertant application of excessive herbicide. For example, because a spray nozzle does not distribute the herbicide evenly.

Therefore, there is an ongoing search in the art to create more effective and more selective herbicidal agents for the selective control of grass weeds growing in the presence of crops and ones which give a better margin of safety so that inadvertent uneven application will not cause so much crop damage, perhaps eliminating such damage altogether.

Substituted alkyl ethers of phenoxyphenols are described in Great Britain Patent No. 1,572,125. However, the compounds described in the above-said patent are distinct from the compounds of the present invention. In addition, the compounds of the above-said patent are not particularly suitable for the selective control of blackgrass growing in the presence of crops at low application rates.

U.S. Pat. No. 4,661,149 discloses substituted phenoxypropionaldehyde derivatives which are outside the scope of the present invention.

It is, therefore, an object of the present invention to provide 2-(heteroaryloxyphenoxy)alkylsulfonates which are highly effective herbicidal agents useful for the selective control of grass weed species in the presence of crops.

It is also an object of this invention to provide certain 2-(heteroaryloxyphenoxy)alkylsulfonate herbicides that exhibit at least a 4× margin of safety when applied to blackgrass, barnyardgrass and green foxtail growing in the presence of cereal crops such as wheat and barley and at least a 16× margin of safety when used for the control of blackgrass, barnyardgrass and green foxtail growing in the presence of broadleaf crops such as soybean.

It is another object of this invention to provide a method for selectively controlling grass weeds in the presence of cereal crops utilizing a 2-(heteroaryloxyphenoxy)alkylsulfonate compound.

SUMMARY OF THE INVENTION

The present invention relates to 2-(heteroaryloxyphenoxy)alkylsulfonates which are useful for the selective control of undesirable grass weed species in the presence of crops.

2-(heteroaryloxyphenoxy)alkylsulfonates of the present invention are illustrated as structural formula I:

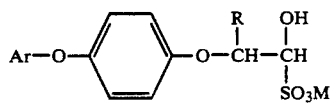

wherein
R is $C_1$–$C_4$ alkyl;
M is hydrogen or an alkali metal, alkaline earth metal, manganese, copper, zinc, cobalt, silver, nickel, ammonium or organic ammonium cation;
Ar is selected from

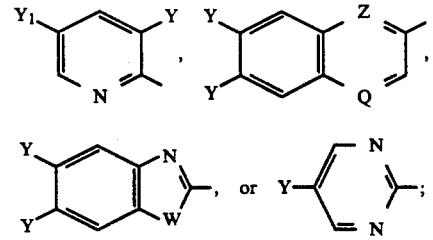

Y is hydrogen, halogen, cyano, $C_1$–$C_4$ alkoxy, $C_1$–$C_4$ alkylthio or $C_1$–$C_4$ alkyl optionally substituted with one to three halogen atoms;
$Y_1$ is halogen, cyano, $C_1$–$C_4$ haloalkyl or nitro;
Z is N or CH;
Q is N or $N^+$—$O^-$
W is O, B, NH or $NR_1$;
$R_1$ is $C_1$–$C_4$ alkyl; and
the racemic diastereomers and chiral diastereomers thereof.

The compounds of the present invention demonstrate selectivity on important agronomic crops such as wheat, barley and soybean while effectively controlling numerous grass weed species such as blackgrass, barnyardgrass, green foxtail and wild oats. It is especially surprising that the herbicides of the present invention are able to control grass weeds while sparing grass or graminaceous crops.

DETAILED DESCRIPTION OF THE INVENTION

Preferred 2-(heteroaryloxyphenoxy)alkylsulfonates of the present invention which are especially useful for the selective control of grass weed species in the presence of crops are illustrated as structural formula II:

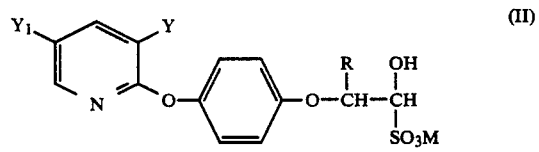

wherein
R is $C_1$–$C_4$ alkyl;
M is hydrogen or an alkali metal, alkaline earth metal, ammonium or organic ammonium cation;
Y is hydrogen, halogen, cyano, $C_1$–$C_4$ alkoxy, $C_1$–$C_4$ alkylthio or $C_1$–$C_4$ alkyl optionally substituted with one to three halogen atoms; and
$Y_1$ is halogen, cyano, $C_1$–$C_4$ haloalkyl or nitro.

Preferred formula II 2-(heteroaryloxyphenoxy)alkylsulfonates of the invention which are especially useful for the selective control of grass weed species such as blackgrass, barnyardgrass and green foxtail in the presence of cereal crops such as wheat and barley are those in which
R is $C_1$–$C_4$ alkyl;
M is hydrogen or a sodium, potassium or ammonium cation;
Y is halogen or $C_1$–$C_4$ alkyl substituted with one to three halogen atoms; and $Y_1$ is halogen or $C_1-C_4$ haloalkyl.

In formulas I and II above, alkali metals include: sodium, potassium and lithium, but sodium is generally preferred. Further, the term "organic ammonium" is defined as a group consisting of a positively charged nitrogen atom joined to from one to four aliphatic groups, each containing from one to sixteen carbon atoms. Exemplary of halogen hereinabove are fluorine, chlorine, bromine and iodine. The term "haloalkyl" is defined as a compound of the following formula $C_pH_qX_r$ where X is halogen and p, q and r are integers such that $q+r=2p+1$.

Certain formula I 2-(heteroaryloxyphenoxy)alkylsulfonates may be prepared by reacting a haloheteroaryl compound of formula III with a dialkali metal salt of hydroquinone in the presence of an organic solvent such as dimethyl sulfoxide to yield the formula IV p-(heteroaryloxy)phenol. The p-(heteroaryloxy)phenol is then reacted with a base such as potassium carbonate and a $C_1-C_4$ alkyl 2-halo-2-($C_1-C_4$ alkyl)acetate in the presence of an organic solvent such as dimethylformamide, at an elevated temperature, to give the $C_1-C_4$ alkyl 2-[p-(heteroaryloxyphenoxy)]-2-($C_1-C_4$ alkyl)acetate of formula V. Reaction of the thus formed acetate with a reducing agent such as diisobutylaluminum hydride and acetic acid in the presence of an organic solvent such as toluene, at a reduced temperature, gives the formula VI 2-[p-(heteroaryloxyphenoxy)]-2-($C_1-C_4$ alkyl)acetaldehyde. Treatment of this acetaldehyde with a bisulfite compound in the presence of an aqueous alcohol solution yields the formula I 2-(heteroaryloxyphenoxy)alkylsulfonate. This reaction scheme is illustrated in Flow Diagram I:

FLOW DIAGRAM I

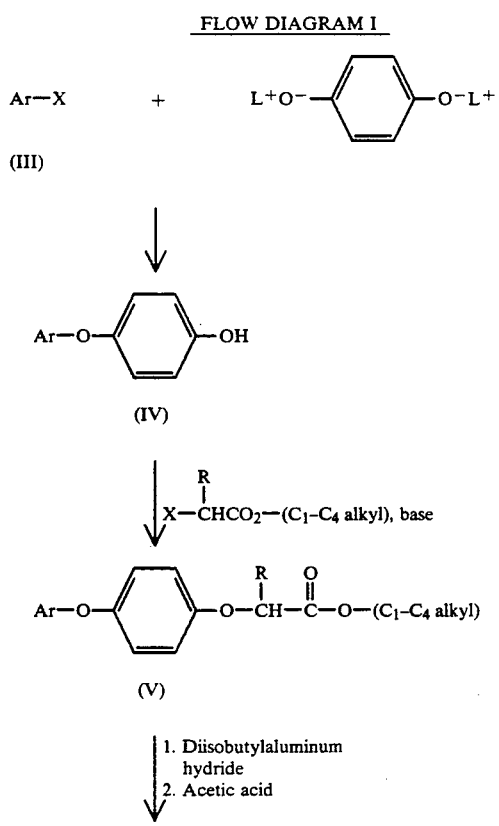

-continued
FLOW DIAGRAM I

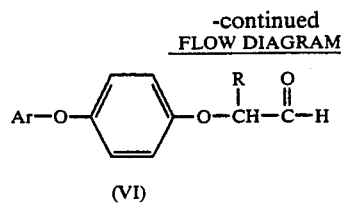

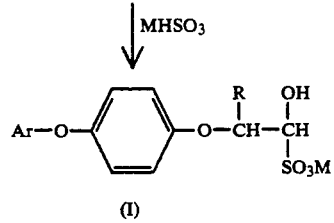

wherein Ar, R and M are as described above for formula I; X is Cl or Br and L is sodium or potassium.

Surprisingly, the 2-(heteroaryloxyphenoxy)alkylsulfonate compounds of the present invention demonstrate selectively on important agronomic crops such as wheat, barley, rice and soybean while effectively controlling numerous grass wheat species. Among the grass weed species controlled by the 2-(heteroaryloxyphenoxy)alkylsulfonates of the present invention are blackgrass, *Alopecurus myosuroides*; barnyardgrass, *Echinochloa crus-galli*; green foxtail, *Setaria viridis*; wild oats, *Avena fatua* and large crabrass, *Digitaria sanguinalis*.

Certain 2-(heteroaryloxyphenoxy)alkylsulfonate compounds of the invention exhibit at least a 4× margin of safety when applied to blackgrass, barnyardgrass and green foxtail growing in the presence of cereal crops such as wheat and barley and at least a 16× margin of safety when used for the control of blackgrass, barnyardgrass and green foxtail growing in the presence of broadleaf crops such as soybean.

The formula I 2-(heteroaryloxyphenoxy)alkylsulfonates of the present invention are effective herbicidal agents useful for the selective control of grass weed species in the presence of cereal, rice and broadleaf crops. These compounds are effective for controlling grass weeds native to both dry land and wet land areas. The compounds are effective in controlling grass weeds when applied to the foliage thereof or to the soil or water containing seeds or other propagating organs of said weeds such as stolons, tubers or rhizomes, at rates of from about 0.032 to 1.0 kg/ha and preferably from about 0.063 to 0.8 kg/ha.

In practice, the formula I 2-(heteroaryloxyphenoxy)alkylsulfonate compounds may be applied to crops in the form of a solid or liquid herbicidal compostion, comprising a herbicidally effective amount of the formula I compound dispersed or dissolved in an inert solid or liquid carrier. The formulations may be applied as preemergence or postemergence treatments. The formulations may also be applied as foliar applications to the cereal crops after the grass weeds have emerged, rendering them eminently suitable for use in grass weed control in wheat and barley.

Advantageously, the water soluble formula I 2-(heteroaryloxyphenoxy)alkylsulfonates can be formulated as emulsifiable concentrates, wettable powders, granular formulations, flowable concentrates and the like.

In order to facilitate a further understanding of the invention, the following examples are presented to illustrate more specific details thereof. The invention is not to be limited thereby except as defined in the claims.

EXAMPLE 1

Preparation of p-[(3,5-Dichloro-2-pyridyl)oxy]phenol

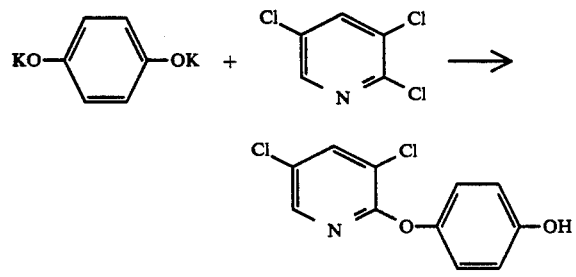

2,3,5-Trichloropyridine (69.32 g, 0.38 mol) and 18-crown-6 (4.0 g, 0.015 mol) are added to a mixture of the dipotassium salt of hydroquinone (prepared from hydroquinone (44.0 g, 0.4 mol) and potassium hydroxide (45.0 g, 0.8 mol)) in dimethyl sulfoxide (700 mL). The reaction mixture is stirred overnight at room temperature, heated at 60° C. for 2½ hours, diluted with water and extracted with ether. The combined organic extracts are washed with water, treated with charcoal, dried over anhydrous magnesium sulfate and concentrated in vacuo to obtain the title product as a white solid (47.23 g, mp 122°-123.5° C.).

EXAMPLE 2

Preparation of Ethyl 2-{p-[(3,5-dichloro-2-pyridyl)oxy]phenoxy}propionate

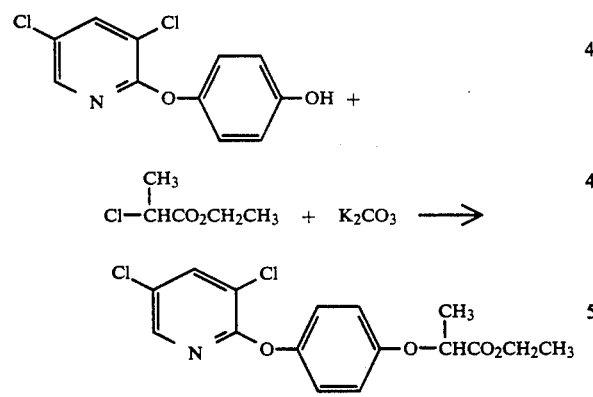

Potassium carbonate (867 g, 6.29 mol) is added to a mixture of p-[(3,5-dichloro-2-pyridyl)oxy]phenol (1,609 g, 6.29 mol), 18-crown-6 (50 g, 0.19 mol) and tetrabutylammonium hydrogen sulfate (50 g, 0.15 mol) in dimethylformamide (20 L). Ethyl 2-chloropropionate (1,380 g, 10.10 mol) is then added and the reaction mixture is stirred for 2 days at 85° C., diluted with water and extracted with methylene chloride. The combined organic extracts are washed sequentially with water, 2% sodium hydroxide solution and water and concentrated in vacuo to give a residue. The residue is dissolved into a 1:1 toluene/heptane solution, washed with 2% sodium hydroxide solution and concentrated in vacuo to obtain the title product as a dark red-brown liquid (1,445 g) which is identified by ¹HNMR spectral analysis.

EXAMPLE 3

Preparation of 2-{p-[(3,5-Dichloro-2-pyridyl)oxy]phenoxy}propionaldehyde

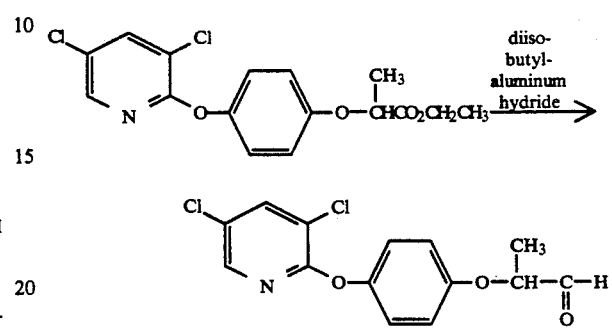

A solution of ethyl 2-{p-[(3,5-dichloro-2-pyridyl)oxy]phenoxy}propionate (1,455 g, 4.06 mol) in toluene (12 L) is cooled to −55° C. under a nitrogen atmosphere and diisobutylaluminum hydride (5.42 L of a 1.0M solution) is added over 2 hours. The reaction mixture is then stirred for 5 hours at −55° C. and glacial acetic acid (1.8 L) is added dropwise, while allowing the mixture to exotherm to 15° C. Heptane (12 L) is added and the mixture is washed sequentially with 5% hydrochloric acid solution, water, saturated sodium bicarbonate solution and water and concentrated in vacuo to obtain the title product as a yellow-orange liquid (1,159 g) which is identified by ¹HNMR spectral analysis.

EXAMPLE 4

Preparation of Sodium 2-{p-[(3,5-dichloro-2-pyridyl)-oxy]phenoxy}-1-hydroxy-1-propanesulfonate

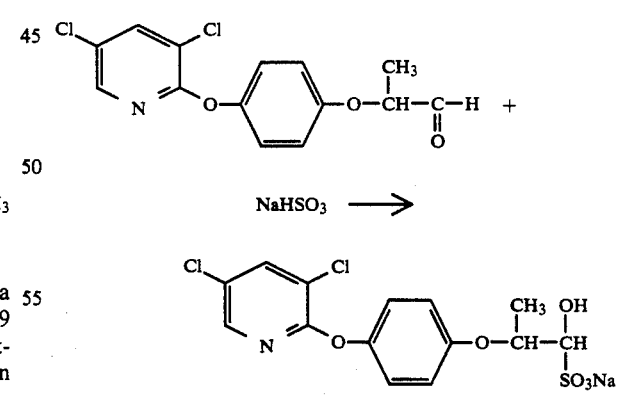

A solution of 2-{p-[(3,5-dichloro-2-pyridyl)-oxy]phenoxy}propionaldehyde (25.38 g, 0.0813 mol) in methanol (300 mL) is added dropwise to a solution of sodium bisulfite (10.2 g, 0.0976 mol) in water (100 mL). The reaction mixture is stirred for 4 days at room temperature and filtered. The filter cake is dried in a vacuum oven overnight to obtain the title product as a white solid (24.6 g, mp 172°-173° C.).

EXAMPLE 5

Preemergence Herbicidal Evaluations

The preemergence herbicidal activity is demonstrated by the following tests. Seeds or propagating organs of each plant species are separately mixed with potting soil and planted on top of approximately one inch of soil in separate pint cups. After planting, the cups are sprayed with an aqueous solution containing the test compound in sufficient quantity to provide the equivalent of about 0.032 to 1.0 kilograms per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved, the data are averaged.

| PLANT SPECIES EMPLOYED IN HERBICIDAL EVALUATION | | |
|---|---|---|
| HEADER ABB | COMMON NAME | SCIENTIFIC NAME |
| | (HAIRY) LARGE | SANGUINALIS, (L) SCOP |
| GREEN FOX | FOXTAIL, GREEN | SETARIA VIRIDIS, (L) BEAUV |
| WILD OATS | OAT, WILD | AVENA FATUA, L. |
| QUACKGRASS | QUACKGRASS | AGROPYRON REPENS, (L) BEAUV. |
| RYE GRASS | RYEGRASS SP. | LOLIUM SP. |
| SOYBEAN WI | SOYBEAN WILLIAMS | GLYCINE MAX |
| S WHT KATE | WHEAT, SPRING CV. KATEPWA | TRITICUM AESTIVUM |
| BRLYBNZA | BARLEY, SPRING CV. BONANZA | HORDEUM VULGARE |
| RICE, TEBON | RICE CV. TEBONNET | ORYZA SATIVA |

TABLE I

Herbicidal Tests via Preemergence Application of Sodium 2-{p-[(3,5-dichloro-2-pyridyl)oxy]phenoxy}-1-hydroxy-1-propanesulfonate

| RATE (kg/ha) | BARNY ARDGR | BLACK GRASS | LARGE CRAB | GREEN FOX | WILD OATS | QUACK GRASS | RYE G RASS | SOYBE AN WI | S WHT KATE | BRLYB NZA | RICE, TEBON |
|---|---|---|---|---|---|---|---|---|---|---|---|
| 1.000 | 9.0 | 9.0 | 9.0 | 9.0 | 9.0 | 9.0 | 9.0 | 0.0 | 7.0 | 7.0 | 9.0 |
| .500 | 9.0 | 9.0 | 9.0 | 9.0 | 7.0 | 9.0 | 9.0 | 0.0 | 7.5 | 4.5 | 9.0 |
| .250 | 9.0 | 9.0 | 9.0 | 9.0 | 6.0 | 9.0 | 9.0 | 0.0 | 3.0 | 2.5 | 7.0 |
| .125 | 9.0 | 9.0 | 8.5 | 9.0 | 4.0 | 4.5 | 8.5 | 0.0 | 2.0 | 2.5 | 9.0 |
| .063 | 8.0 | 8.0 | 7.5 | 8.0 | 0.0 | 3.0 | 3.0 | 0.0 | 0.0 | 0.0 | 2.0 |
| .032 | 7.0 | 6.5 | 6.0 | 4.5 | 1.5 | 1.5 | 2.0 | 0.0 | 0.0 | 0.0 | 0.0 |

Plant species employed in these evaluations are reported by header abbreviation, common name and scientific name.

Herbicide Rating Scale

Results of herbicide evaluation are expressed on a rating scale (0-9). The scale is based upon a visual observation of plant stand, vigor, malformation, size, chlorosis and overall appearance as compared with a control.

| Rating | Meaning | % Control Compared To Check |
|---|---|---|
| 9 | Complete kill | 100 |
| 8 | Approaching Complete Kill | 91-99 |
| 7 | Good Herbicidal Effect | 80-90 |
| 6 | Herbicidal Effect | 65-79 |
| 5 | Definite Injury | 45-64 |
| 4 | Injury | 30-44 |
| 3 | Moderate Effect | 16-29 |
| 2 | Slight Effect | 6-15 |
| 1 | Trace Effect | 1-5 |
| 0 | No Effect | 0 |

| PLANT SPECIES EMPLOYED IN HERBICIDAL EVALUATION | | |
|---|---|---|
| HEADER ABB | COMMON NAME | SCIENTIFIC NAME |
| BARNYARDGR | BARNYARDGRASS | ECHINOCHLOA CRUS-GALLI (L) BEAU |
| BLACKGRASS | BLACKGRASS | ALOPECURUS MYOSUROIDES |
| LARGE CRAB | CRABGRASS, | DIGITARIA |

EXAMPLE 6

Weed Control of Grass Weeds and Tolerance of Crops Postemergence

The postemergence herbicidal activity is demonstrated by the following tests. Seedling plants are grown in jiffy flats for about two weeks. The plants are then sprayed with the selected aqueous acetone solution containing the test compound in sufficient quantity to provide the equivalent of about 0.63 to 1.0 kilograms per hectare. These solutions also contain 0.5% TWEEN® 20, a polyoxyethylene sorbitan monolaurate surfactant of Atlas Chemical Industries.

After spraying, the plants are placed on greenhouse benches and are cared for in the usual manner, commensurate with conventional greenhouse practices. From four to five weeks after treatment, the seedling plants are examined and rated according to the rating system provided in Example 5 above. The data obtained are recorded in Table II below.

Crop Safe Rate and Weed Control Rate

Crop safe rate is the highest rate (in g/ha) with a crop herbicide rating of 0 or 1. Weed control rate is the lowest rate (in g/ha) with a herbicide rating of 8 or 9. The crop safe and weed control rates are reported in Table III below.

Selectivity Margins

Selectivity margin for wheat, barley, soybean and rice is the plant safe rate (g/ha) divided by weed control rate (g/ha). The selectivity margins are reported in Table IV below.

TABLE II

Herbicidal Tests via Postemergence Application of Sodium 2-{p-[(3,5-dichloro-2-pyridyl)oxy]phenoxy}-1-hydroxy-1-propanesulfonate

| RATE (kg/ha) | BARNY ARDGR | BLACK GRASS | LARGE CRAB | GREEN FOX | WILD OATS | QUACK GRASS | RYE GRASS | SOYBE AN WI | S WHT KATE | BRLYB NZA | RICE, TEBON |
|---|---|---|---|---|---|---|---|---|---|---|---|
| 1.000 | 9.0 | 9.0 | 9.0 | 9.0 | 9.0 | 4.0 | 9.0 | 0.0 | 5.0 | 3.0 | 9.0 |
| .500 | 9.0 | 9.0 | 9.0 | 9.0 | 9.0 | 2.0 | 9.0 | 0.0 | 3.0 | 2.0 | 9.0 |
| .250 | 9.0 | 9.0 | 9.0 | 9.0 | 2.0 | 0.0 | 6.0 | 0.0 | 0.0 | 0.0 | 8.0 |
| .125 | 9.0 | 7.0 | 9.0 | 9.0 | 2.0 | 0.0 | 4.0 | 0.0 | 0.0 | 0.0 | 6.0 |
| .063 | 9.0 | 8.0 | 6.0 | 9.0 | 3.0 | 0.0 | 0.0 | 0.0 | 0.0 | 0.0 | 1.0 |

TABLE III

Crop Safe Rate and Weed Control Rate for Plants Treated via Postemergence Application of Sodium 2-{p-[(3,5-dichloro-2-pyridyl)oxy]phenoxy}-1-hydroxy-1-propanesulfonate

| Crop | Safe Rate (g/ha) | Weed | Control Rate (g/ha) |
|---|---|---|---|
| Wheat, spring cv. Katepwa | 250 | Blackgrass | 63 |
| Barley, spring cv. Bonanza | 250 | Barnyardgrass | 63 |
| Rice cv. Tebonnet | 63 | Foxtail, green | 63 |
| Soybean Williams | 1,000 | | |

TABLE IV

Selectivity Margins For Plants Treated via Postemergence Application of Sodium 2-{p-[(3,5-dichloro-2-pyridyl)oxy]phenoxy}-1-hydroxy-1-propanesulfonate

| | Selectivity Margin | | |
|---|---|---|---|
| Crop | Blackgrass | Barnyardgrass | Foxtail, green |
| Wheat, spring cv. Katepwa | 4 | 4 | 4 |
| Barley, spring cv. Bonanza | 4 | 4 | 4 |
| Rice cv. Tebonnet | 1 | 1 | 1 |
| Soybean Williams | 16 | 16 | 16 |

We claim:

1. A 2-(heteroaryloxyphenoxy)alkylsulfonate compound having the structural formula

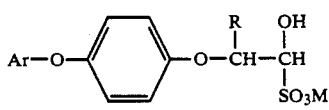

wherein
R is $C_1$-$C_4$ alkyl;
M is hydrogen or an alkali metal, alkaline earth metal, manganese, copper, zinc, cobalt, silver, nickel, ammonium or organic ammonium cation;
Ar is

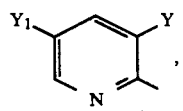

Y is hydrogen, halogen, cyano, $C_1$-$C_4$ alkoxyl, $C_1$-$C_4$ alkylthio or $C_1$-$C_4$ alkyl optionally substituted with one to three halogen atoms;
$Y_1$ is halogen, cyano, $C_1$-$C_4$ haloalkyl or nitro;
the racemic diastereomers and chiral diastereomers thereof.

2. The compound according to claim 1 wherein
M is hydrogen or an alkali metal, alkaline earth metal, ammonium or organic ammonium cation.

3. The compound according to claim 2 wherein
M is hydrogen or a sodium, potassium or ammonium cation;
Y is halogen or $C_1$-$C_4$ alkyl substituted with one to three halogen atoms; and
$Y_1$ is halogen or $C_1$-$C_4$ haloalkyl.

4. The compound according to claim 3, sodium 2-{p-[(3,5-dichloro-2-pyridyl)oxy]phenoxy}-1-hydroxy-1-propanesulfonate.

5. A method for the selective control of undesirable grass weed species in the presence of cereal, rice and broadleaf crops which comprises applying to the foliage and stems of the crops and undesirable vegetation growing in the presence thereof or to the soil or water containing seeds or other propagating organs of the undesirable vegetation in which the crops are growing, a herbicidally effective amount of a compound having the structure

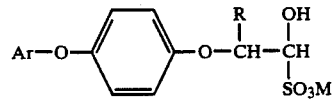

wherein
R is $C_1$-$C_4$ alkyl;
M is hydrogen or an alkali metal, alkaline earth metal, maganese, copper, zinc, cobalt, silver, nickel, ammonium or organic ammonium cation;
Ar is

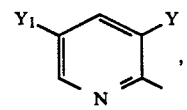

Y is hydrogen, halogen, cyano, $C_1$-$C_4$ alkoxyl, $C_1$-$C_4$ alkylthio or $C_1$-$C_4$ alkyl optionally substituted with one to three halogen atoms;
$Y_1$ is halogen, cyano, $C_1$-$C_4$ haloalkyl or nitro;
the racemic diastereomers and chiral diastereomers thereof.

6. The method according to claim 5 wherein
M is hydrogen or an alkali metal, alkaline earth metal, ammonium or organic ammonium cation and
$Y_1$ is halogen, cyano, $C_1$-$C_4$ haloalkyl or nitro.

7. The method according to claim 6 wherein the compound is sodium 2-{p-[(3,5-dichloro-2-pyridyl)oxy]phenoxy}-1-hydroxy-1-propanesulfonate.

8. The method according to claim 5 wherein the undesirable vegetation is blackgrass, barnyardgrass and green foxtail and the crops are wheat, barley, soybean or rice.

9. The method according to claim 5 wherein the compound is applied to the crops and undesirable vegetation or to the soil or water containing seeds or other propagating organs of the undesirable vegetation, at the rate of about 0.032 kg/ha to 1.0 kg/ha.

10. A herbicidal composition comprising an inert carrier and an effective amount of a 2-(heteroaryloxyphenoxy)alkylsulfonate compound as described in claim 1.

* * * * *